(12) United States Patent  
Neidhart et al.

(10) Patent No.: US 7,265,109 B2
(45) Date of Patent: Sep. 4, 2007

(54) THIAZOLE DERIVATIVES

(75) Inventors: Werner Neidhart, Hagenthal le Bas (FR); Matthias Heinrich Nettekoven, Grenzach-Wyhlen (DE); Philippe Pflieger, Schwoben (FR); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 490 days.

(21) Appl. No.: 10/915,190

(22) Filed: Aug. 10, 2004

(65) Prior Publication Data

US 2005/0038073 A1    Feb. 17, 2005

(30) Foreign Application Priority Data

Aug. 12, 2003    (EP)    ................. 03017633

(51) Int. Cl.
*A61K 31/5377* (2006.01)
*A61K 31/454* (2006.01)
*A61K 31/427* (2006.01)
*C07D 295/18* (2006.01)
*C07D 417/14* (2006.01)
*C07D 413/14* (2006.01)
*C07D 277/20* (2006.01)

(52) U.S. Cl. ............. 514/230.8; 514/318; 514/326; 514/370; 544/130; 546/193; 546/209; 548/194

(58) Field of Classification Search ......... 514/230.8, 514/318, 326, 370; 544/130; 546/193, 209; 548/194
See application file for complete search history.

(56) References Cited

U.S. PATENT DOCUMENTS

| | | |
|---|---|---|
| 4,598,089 A | 7/1986 | Hadvary et al. |
| 4,776,409 A | 10/1988 | Manchak, Jr. |
| 4,844,807 A | 7/1989 | Manchak, Jr. |
| 4,844,839 A | 7/1989 | Manchak, Jr. |
| 4,931,463 A | 6/1990 | Barbier et al. |
| 4,983,746 A | 1/1991 | Barbier et al. |
| 5,175,186 A | 12/1992 | Barbier et al. |
| 5,245,056 A | 9/1993 | Karpf et al. |
| 5,246,960 A | 9/1993 | Barbier et al. |
| 5,399,720 A | 3/1995 | Karpf et al. |
| 6,004,996 A | 12/1999 | Shah et al. |
| 6,569,856 B2 | 5/2003 | Marzabadi et al. |
| 2005/0101595 A1* | 5/2005 | Chu et al. ............ 514/217.09 |

FOREIGN PATENT DOCUMENTS

| | | |
|---|---|---|
| EP | 185359 A2 | 12/1985 |
| EP | 189577 | 12/1985 |
| EP | 185359 B1 | 12/1991 |
| EP | 524495 | 10/1996 |
| EP | 443449 | 5/1997 |
| WO | WO99/34786 | 7/1999 |
| WO | WO99/62892 | 12/1999 |
| WO | WO 00/09122 | 2/2000 |
| WO | WO 00/09123 | 2/2000 |
| WO | WO 01/64675 | 9/2001 |
| WO | WO 03/011843 | 2/2003 |
| WO | WO 03/072577 | 9/2003 |

* cited by examiner

*Primary Examiner*—Kamal A. Saeed
*Assistant Examiner*—Nyeemah Grazier
(74) *Attorney, Agent, or Firm*—George W. Johnston; Dennis P. Tramaloni; Samuel H. Megerditchian

(57) ABSTRACT

Compounds of formula I (I)

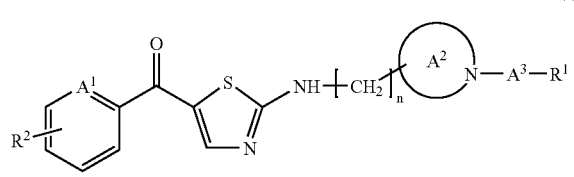

as well as pharmaceutically acceptable salts and esters thereof, wherein the substituents have the significance given in the specification, and the compounds are neuropeptide Y(NPY) antagonists which are useful in the treatment of obesity.

29 Claims, No Drawings

THIAZOLE DERIVATIVES

BACKGROUND OF THE INVENTION

Neuropetide Y is a 36 amino acid peptide that is widely distributed in the central and peripheral nervous systems. This peptide mediates a number of physiological effects through its various receptor subtypes. Studies in animals have shown that neuropeptide Y is a powerful stimulus of food intake, and it has been demonstrated that activation of neuropeptide Y Y5 receptors results in hyperphagia and decreased thermogenesis. Therefore compounds that antagonise neuropetide Y at the Y5 receptor subtype represent an approach to the treatment of eating disorders such as obesity and hyperphagia.

The current approach is aiming at medical intervention to induce weight loss or prevention of weight gain. This is achieved by interfering with appetite control, which is mediated by the Hypothalamus, an important brain region proven to control food intake. Herein, neuropeptide Y (NPY) has been proven to be one of the strongest central mediators of food intake in several animal species. Increased NPY levels result in profound food intake. Various receptors of neuropeptide Y (NPY) have been described to play a role in appetite control and weight gain. Interference with these receptors is likely to reduce appetite and consequently weight gain. Reduction and long-term maintenance of body weight can also have beneficial consequences on co-associated risk factors such as arthritis, cardiovascular diseases, diabetes and renal failure.

SUMMARY OF THE INVENTION

The present invention provides a compound of formula I

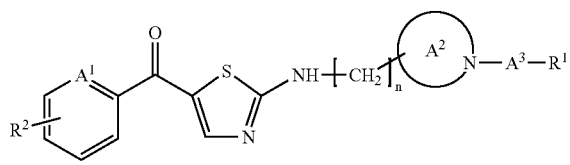

wherein

R$^1$ is selected from the group consisting of aryl; substituted aryl; heterocyclyl which is a 5- to 10 membered heterocyclic ring which has at least one ring hetero atom selected from nitro, oxygen and sulfur; substituted heterocyclyl; amino; and alkoxy; wherein substituted aryl is aryl which is substituted with a group selected from the group consisting of halogen, trifluoromethyl, trifluoromethoxy, amino, alkyl, cycloalkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-SO$_2$—, amino-SO$_2$—, and cycloalkyl, and wherein substituted heterocyclyl is heterocyclyl which is substituted on at least one carbon atom with a group selected from the group consisting of cyano, trifluoromethyl, trifluoromethoxy, alkyl-SO$_2$—, amino-SO$_2$—, halogen, alkoxy, hydroxy, amino, cycloalkyl, alkylcarbonyl, aminocarbonyl nitro, alkyl, and alkoxycarbonyl;

R$^2$ is hydrogen, alkyl or halogen;

R$^3$ is alkyl, halogen or trifluoromethyl;

A$^1$ is C—R$^3$ or nitrogen;

A$^2$ is piperidine or pyrrolidine, wherein the nitrogen atom of the piperidine and pyrrolidine ring is attached to A$^3$;

A$^3$ is —S(O)$_2$— or —C(O)—;

n is zero, 1 or 2;

or a pharmaceutically acceptable salt or ester thereof.

The compounds of formula I and their pharmaceutically acceptable salts and esters are neuropeptide ligands, for example neuropeptide receptor antagonists and in particular, they are selective neuropeptides Y Y5 receptor antagonists.

DETAILED DESCRIPTION OF THE INVENTION

The present invention provides a compound of formula I

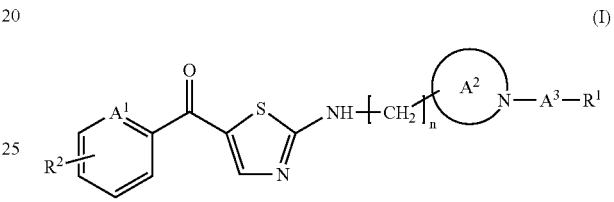

wherein

R$^1$ is selected from the group consisting of aryl; substituted aryl; heterocyclyl which is a 5- to 10 membered heterocyclic ring which has at least one ring hetero atom selected from nitro, oxygen and sulfur; substituted heterocyclyl; amino; and alkoxy; wherein substituted aryl is aryl which is substituted with a group selected from the group consisting of halogen, trifluoromethyl, trifluoromethoxy, amino, alkyl, cycloalkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-SO$_2$—, amino-SO$_2$—, and cycloalkyl, and wherein substituted heterocyclyl is heterocyclyl which is substituted on at least one carbon atom with a group selected from the group consisting of cyano, trifluoromethyl, trifluoromethoxy, alkyl-SO$_2$—, amino-SO$_2$—, halogen, alkoxy, hydroxy, amino, cycloalkyl, alkylcarbonyl, aminocarbonyl nitro, alkyl, and alkoxycarbonyl;

R$^2$ is hydrogen, alkyl or halogen;

R$^3$ is alkyl, halogen or trifluoromethyl;

A$^1$ is C—R$^3$ or nitrogen;

A$^2$ is piperidine or pyrrolidine, wherein the nitrogen atom of the piperidine and pyrrolidine ring is attached to A$^3$;

A$^3$ is —S(O)$_2$— or —C(O)—;

n is zero, 1 or 2;

or a pharmaceutically acceptable salt or ester thereof.

The compounds of formula I and their pharmaceutically acceptable salts and esters are neuropeptide ligands, for example neuropeptide receptor antagonists and in particular, they are selective neuropeptides Y Y5 receptor antagonists.

Accordingly, the compounds of formula I can be used in the prophylaxis or treatment of arthritis, cardiovascular diseases, diabetes, renal failure and particularly eating disorders and obesity.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalxyl ring with 3 to 6 carbon atoms. Examples of $C_3$-$C_8$ cycloalkyl are cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy, preferably methoxy and ethoxy and most preferred methoxy.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, cycloalkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-$SO_2$—, amino-$SO_2$—, cycloalkyl and the like. Preferred is phenyl or naphthyl, particularly phenyl optionally substituted with one to three, preferably one or two substituents independently selected from alkyl, halogen, alkoxy, trifluoromethoxy, nitro and trifluoromethyl.

The term "heterocyclyl", alone or in combination, signifies aromatic 5- to 10-membered heterocycle which comprises one or more, preferably one or two, particularly preferred one hetero atom selected from nitrogen, oxygen and sulfur. It can be substituted on one or more carbon atoms by cyano, trifluoromethyl, trifluoromethoxy, alkyl-$SO_2$—, amino-$SO_2$—, halogen, alkoxy, hydroxy, amino, cycloalkyl, alkylcarbonyl, aminocarbonyl nitro, alkyl, and/or alkoxycarbonyl. Preferred heterocydyl cycles are pyrrolidinyl and thiophenyl particularly, wherein thiophenyl and pyrrolidinyl are optionally substituted with one to three substituents, preferably one or two, independently selected from alkyl, alkoxy, trifluoromethyl, trifluoromethoxy, nitro and halogen.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —$NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "halogen" signifies fluorine, chlorine, bromine or iodine and preferably fluorine, chlorine or bromine.

The term "carbonyl", alone or in combination signifies the —C(O)— group.

The term "nitro", alone or in combination signifies the —$NO_2$ group.

The term "cyano", alone or in combination signifies the group —CN.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention. In the present invention, esters may be present, for example, where $R^1$ is a ring such as a heterocycle, which is substituted by hydroxy.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The compounds of formula I can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates.

Preferred are the compounds of formula I and pharmaceutically acceptable salts thereof, particularly the compounds of formula I.

Further preferred are the compounds of formula I, wherein $R^1$ is naphthyl, pyrrolidinyl, dialkylamino, morpholinyl, alkoxy, phenyl or thiophenyl, wherein phenyl and thiophenyl are optionally substituted with one to three substituents independently selected from alkyl, alkoxy, trifluoromethyl, trifluoromethoxy, nitro and halogen. Particularly preferred are the above compounds of formula I, wherein the term thiophenyl means thiophen-2-yl, thiophen-3-yl or 5-chloro-thiophen-2-yl. Further particularly preferred are the above compounds according to formula I, wherein the term phenyl means 2-fluorophenyl, 3-fluorophenyl, 4-fluorophenyl, 2,4-difluorophenyl, 2-methylphenyl, 2,5-dimethylphenyl, 2-methyl-5-fluorophenyl, 3-methoxyphenyl, 4-methoxyphenyl, 4-trifluoromethoxyphenyl, 2-chloro-4-trifluoromethylphenyl, 4-chlorophenyl, 4-nitrophenyl or 2-methoxy-5-methylphenyl.

Another preferred embodiment of the present invention are compounds according to formula I, wherein $R^1$ is thiophenyl, chloro-thiophenyl, naphthyl, pyrrolidinyl, dimethylamino, morpholinyl, tert-butoxy or phenyl substituted with one or two substituents independently selected from fluoro, chloro, methyl, ethyl, methoxy, ethoxy, trifluoromethoxy, trifluoromethyl and nitro. Particularly preferred are the above compounds of formula I, wherein the term thiophenyl means thiophen-2-yl or thiophen-3-yl. Particularly preferred are the above compounds of formula I, wherein the term chloro-thiophenyl means 5-chloro-thiophen-2-yl. Further particularly preferred are the above compounds according to formula I, wherein the term phenyl means 2-fluorophenyl, 3-fluorophenyl, 4-fluorophenyl, 2,4-difluorophenyl, 2-methylphenyl, 2,5-dimethylphenyl, 2-methyl-5-fluorophenyl, 3-methoxyphenyl, 4-methoxyphenyl, 4-trifluoromethoxyphenyl, 2-chloro-4-trifluoromethylphenyl, 4-chlorophenyl, 4-nitrophenyl or 2-methoxy-5-methylphenyl.

Also preferred are the compounds of formula I, wherein $R^2$ is hydrogen.

Preferred are the compounds according to formula I, wherein $A^1$ is nitrogen.

Further preferred are the compounds of formula I, wherein $A^1$ is C-$R^3$. Particularly preferred are those compounds of formula I, wherein $R^3$ is methyl, ethyl or trifluoromethyl. Further particularly preferred are the compounds according to formula I, wherein $A^1$ is C-$R^3$ and, wherein $R^3$ is alkyl, preferably methyl or ethyl. Particularly preferred are those compounds of formula I, wherein $R^3$ is methyl.

Another preferred aspect of the present invention are the compounds of formula I, wherein $A^3$ is —C(O)—. Particularly preferred are those compounds of formula I, wherein $A^3$ is —S(O)$_2$—.

Further preferred are the compounds according to formula I, wherein $A^2$ is pyrrolidine, wherein the nitrogen atom of the pyrrolidine ring is attached to $A^3$. Particularly preferred are those compounds of formula I, wherein $A^2$ is piperidine, wherein the nitrogen atom of the piperidine ring is attached to $A^3$.

Preferred are compounds of formula I, wherein n is zero or 1. Particularly preferred are those, wherein n is zero.

Examples of preferred compounds of formula (I) are:

1. (2-{[1-(thiophene-2-sulfonyl)-piperidin-4-ylmethyl]-amino}-thiazol-5-yl)-o-tolyl-methanone 2. (2-{[1-(thiophene-3-sulfonyl)-piperidin-4-ylmethyl]-amino}-thiazol-5-yl)-o-tolyl-methanone 3. (2-{[1-(5-chloro-thiophene-2-sulfonyl)-piperidin-4-ylmethyl]-amino}-thiazol-5-yl)-o-tolyl-methanone;

4. (2-{[1-(2-fluoro-benzenesulfonyl)-piperidin-4-ylmethyl]-amino}-thiazol-5-yl)-o-tolyl -methanone;

5. (2-{[1-(3-fluoro-benzenesulfonyl)-piperidin-4-ylmethyl]-amino}-thiazol-5-yl)-o-tolyl -methanone;

6. (2-{[1-(4-fluoro-benzenesulfonyl)-piperidin-4-ylmethyl]-amino}-thiazol-5-yl)-o-tolyl -methanone;

7. (2-{[1-(2,4-difluoro-benzenesulfonyl)-piperidin-4-ylmethyl]-amino}-thiazol-5-yl)-o-tolyl -methanone;

8. (2-{[1-(toluene-2-sulfonyl)-piperidin-4-ylmethyl]-amino}-thiazol-5-yl)-o-tolyl-methanone;

9. (2-{[1-(2,5-dimethyl-benzenesulfonyl)-piperidin-4-ylmethyl]-amino}-thiazol-5-yl)-o-tolyl -methanone;

10. (2-{[1-(5-fluoro-2-methyl-benzenesulfonyl)-piperidin-4-ylmethyl]-amino}-thiazol-5-y -methanone;

11. (2-{[1-(3-methoxy-benzenesulfonyl)-piperidin-4-ylmethyl]-amino}-thiazol-5yl)-o-tolyl-methanone;

12. (2-{[1-(4-methoxy-benzenesulfonyl)-piperidin-4-ylmethyl]-amino}-thiazol-5-yl)-o-tolyl-methanone;

13. o-tolyl-(2-{[1-(4-trifluoromethoxy-benzenesulfonyl)-piperidin-4-ylmethyl]-amino}-thiazol-5-yl)-methanone;

14. (2-{[1-(2-chloro-4-trifluoromethyl-benzenesulfonyl)-piperidin-4-ylmethyl]-amino}-thiazol-5-yl)-o-tolyl-methanone;

15. (2-{[1-(4-chloro-benzenesulfonyl)-piperidin-4-ylmethyl]-amino}-thiazol-5-yl)-o-tolyl-methanone;

16. (2-{[1-(4-nitro-benzenesulfonyl)-piperidin-4-ylmethyl]-amino}-thiazol-5-yl)-o-tolyl-methanone;

17. (2-{[1-(pyrrolidine-1-sulfonyl)-piperidin-4-ylmethyl]-amino}-thiazol-5-yl)-o-tolyl-methanone;

18. 4-{[5-(2-methyl-benzoyl)-thiazol-2-ylamino]-methyl}-piperidine-1-sulfonic acid dimethylamide;

19. (2-{[1-(morpholine-4-sulfonyl)-piperidin-4-ylmethyl]-amino}-thiazol-5-yl)-o-tolyl-methanone;

20. (2-{2-[1-(thiophene-3-sulfonyl)-piperidin-2-yl]-ethylamino}-thiazol-5-yl)-o-tolyl-methanone;

21. (2-{2-[1-(3-fluoro-benzenesulfonyl)-piperidin-2-yl]-ethylamino}-thiazol-5-yl)-o-tolyl-methanone;

22. (S)-2-{[5-(2-ethyl-benzoyl)-thiazol-2-ylamino]-methyl}-pyrrolidine-1-carboxylic acid tert-butyl ester;

23. (S)-2-{[5-(2-trifluoromethyl-benzoyl)-thiazol-2-ylamino]-methyl}-pyrrolidine-1-carboxylic acid tert-butyl ester;

24. (S)-(2-ethyl-phenyl)-(2-{[1-(thiophene-2-sulfonyl)-pyrrolidin-2-ylmethyl]-amino}-thiazol-5-yl)-methanone;

25. (S)-(2-{[1-(thiophene-2-sulfonyl)-pyrrolidin-2-ylmethyl]-amino}-thiazol-5-yl)-(2-trifluoromethyl-phenyl)-methanone;

26. (S)-(2-{[1-(naphthalene-1-sulfonyl)-pyrrolidin-2-ylmethyl]-amino}-thiazol-5-yl)-(2-trifluoromethyl-phenyl)-methanone;

27. 4-[5-(2-ethyl-benzoyl)-thiazol-2-ylamino]-piperidine-1-carboxylic acid tert-butyl ester;

28. 4-[5-(2-methyl-benzoyl)-thiazol-2-ylamino]-piperidine-1-carboxylic acid tert-butyl ester;

29. 4-[5-(2-trifluoromethyl-benzoyl)-thiazol-2-ylamino]-piperidine-1-carboxylic acid tert-butyl ester;

30. 4-[5-(pyridine-2-carbonyl)-thiazol-2-ylamino]-piperidine-1-carboxylic acid tert-butyl ester;

31. (2-ethyl-phenyl)-{2-[1-(naphthalene-1-sulfonyl)-piperidin-4-ylamino]-thiazol-5-yl}-methanone;

32. (2-ethyl-phenyl)-{2-[1-(thiophene-2-sulfonyl)-piperidin-4-ylamino]-thiazol-5-yl}-methanone;

33. (2-ethyl-phenyl)-{2-[1-(2-methoxy-5-methyl-benzenesulfonyl)-piperidin-4-ylamino]-thiazol-5-yl}-methanone;

34. {2-[1-(naphthalene-1-sulfonyl)-piperidin-4-ylamino]-thiazol-5-yl}-pyridin-2-yl-methanone;

35. pyridin-2-yl-{2-[1-(thiophene-2-sulfonyl)-piperidin-4-ylamino]-thiazol-5-yl}-methanone;

36. {2-[1-(2-methoxy-5-methyl-benzenesulfonyl)-piperidin-4-ylamino]-thiazol-5-yl}-pyridin-2-yl-methanone;

37. {2-[1-(naphthalene-1-sulfonyl)-piperidin-4-ylamino]-thiazol-5-yl}-(2-trifluoromethyl-phenyl)-methanone;

38. {2-[1-(thiophene-2-sulfonyl)-piperidin-4-ylamino]-thiazol-5-yl}-(2-trifluoromethyl-phenyl)-methanone;

39. {2-[1-(2-methoxy-5-methyl-benzenesulfonyl)-piperidin-4-ylamino]-thiazol-5-yl}-(2-trifluoromethyl-phenyl)-methanone;

40. {2-[1-(naphthalene-1-sulfonyl)-piperidin-4-ylamino]-thiazol-5-yl}-o-tolyl-methanone;

41. {2-[1-(thiophene-2-sulfonyl)-piperidin-4-ylamino]thiazol-5-yl}-o-tolyl-methanone; and 42. {2-[1-(2-methoxy-5-methyl-benzenesulfonyl)-piperidin-4-ylamino]-thiazol-5-yl}-o-tolyl-methanone.

Examples of particularly preferred compounds of formula (I) are:

4-{[5-(2-methyl-benzoyl)-thiazol-2-ylamino]-methyl}-piperidine-1-sulfonic acid dimethylamide;

(2-ethyl-phenyl)-{2-[1-(thiophene-2-sulfonyl)-piperidin-4-ylamino]-thiazol-5-yl}-methanone; and {2-[1-(thiophene-2-sulfonyl)-piperidin-4-ylamino]-thiazol-5-yl}-o-tolyl-methanone.

Processes for the manufacture of compounds of formula I are an object of the invention.

The preparation of compounds of formula I of the present invention may be carried out in sequential or convergent synthetic routes. Syntheses of the invention are shown in the following Schemes. The skills required for carrying out the reaction and purification of the resulting products are known to those in the art. The substituents and indices used in the following description of the processes have the significance given above unless indicated to the contrary.

Compounds of general formula I can be prepared according to scheme 1 as follows:

a) Boc-protected piperidine amines and Boc-protected pyrrolidine amines IA, which are either commercially available or described previously in the literature, can be converted to thioureas by various procedures described in the art. However we find it convenient to react IA with benzoylisothiocanate in a solvent and subsequenty basic removal of the benzoyl group to liberate the thioureas IB. For reaction conditions described in literature affecting such a reaction see for example: Tetrahedron 1963, 19, 1603.

b) Thioureas IB can be conveniently reacted with with N,N-dimethylformamide dimethyl acetal in the presence or the absence of a solvent in order to access the respective dimethylaminomethylene-thioureido derivatives IC. There is no particular restriction on the nature of the solvent to be employed, provided that it has no adverse effect on the reaction or the reagents involved and that it can dissolve the reagents, at least to some extent. Examples for suitable solvents include: DMF and dioxane and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the dimethylaminomethylene-thioureido derivatives IC. For reaction conditions described in literature affecting such a reaction see for example: Heterocycles 11, 313-318; 1978.

c) Dimethylaminomethylene-thioureido derivatives IC can be converted to thiazole derivatives ID by reaction of IC with α-bromoketones (a known compound or compound prepared by known methods. The source for α-bromoketones employed is indicated as appropriate) in a solvent such as ethanol, and the like, in the presence or the absence of a base. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, or dioxane, methanol, ethanol and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the thiazole derivatives ID. For reaction conditions described in literature affecting such a reaction see for example: J. Heterocycl. Chem., 16(7), 1377-83; 1979. The resulting compound of formula ID is a compound of the present invention and may be the desired product.

d) Alternatively it may be subjected to consecutive reactions like removal of the Boc-protecting group via methods described widely in literature to yield the desired thiazole derivatives IE. We find it convenient to remove the Boc-protecting group from ID under acidic conditions in the presence or absence of a solvent. There is no particular restriction on the nature of the solvent to be employed, provided that it has no adverse effect on the reaction or the reagents involved and that it can dissolve the reagents, at least to some extent. Examples for suitable solvents include: dioxane, THF, and the like. There is no particular restriction on the nature of the acid used in this stage, and any acid commonly used in this type of reaction may equally be employed here. Examples of such acids include HCl, TFA and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield thiazole IE or the respective salt thereof. For reaction conditions described in literature affecting such reactions see for example: Heterocycles 1991, 32, 1699.

e) Sulfonamides, sulfonic acid derivatives, amides, carbamates and ureas can be prepared from suitable starting materials according to methods known in the art. The conversion of the amino-moiety in IE to access sulfonamides, sulfonic acid derivatives, amides, carbamates and ureas can be affected by methods described in literature. For example the conversion of the amine derivatives IE or their respective salts to access compounds of the general formula I is affected by reaction of IE with suitable acid chlorides, sulfonyl chlorides, sulfamoyl chlorides, isocyanates, chloroformates, or carbonate esters (compounds known or compound prepared by known methods) respectively in the presence or the absence of a solvent and in the presence of a base. There is no particular restriction on the nature of the solvent to be employed, provided that it has no adverse effect on the reaction or the reagents involved and that it can dissolve the reagents, at least to some extent. Examples for suitable solvents include: DCM, chloroform, dioxane, MeOH or THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield thiazole derivatives I. For reaction conditions described in literature affecting such reactions see for example: Comprehensive Organic Transformations: A Guide to Functional Group Preparations, 2nd Edition, Richard C. Larock. John Wiley & Sons, New York, N.Y. 1999

Scheme 1

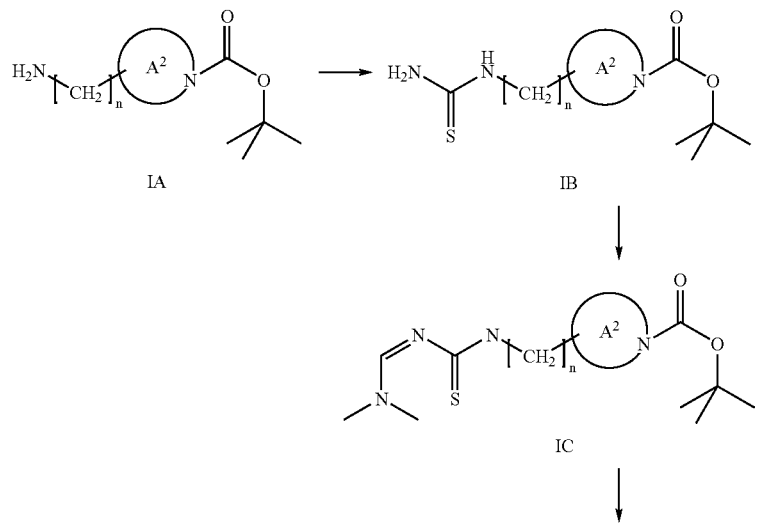

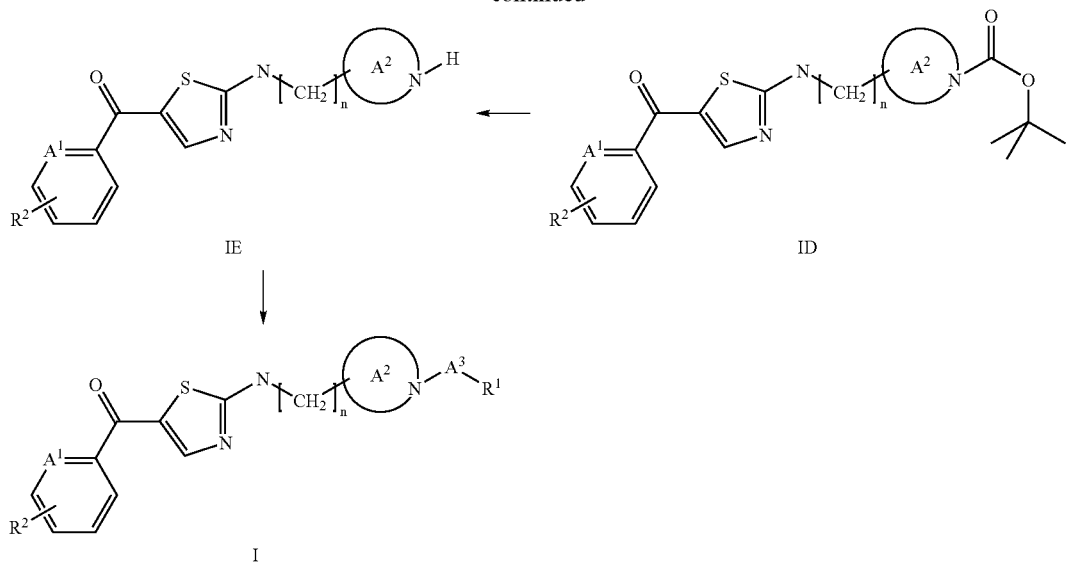

The conversion of a compound of formula I into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The corresponding carboxylate salts can also be prepared from the compounds of formula I by treatment with physiologically compatible bases.

The conversion of compounds of formula I into pharmaceutically acceptable esters or amides can be carried out e.g. by treatment of suited amino or hydroxyl groups present in the molecules with an carboxylic acid such as acetic acid, with a condensating reagent such as benzotriazol-1-yloxytris(dimethylamino)phosphonium hexafluorophosphate (BOP) or N,N-dicylohexylcarbodiimide (DCCI) to produce the carboxylic ester or carboxylic amide.

A preferred process for the preparation of a compound of formula I comprising the reaction of a compound according to formula

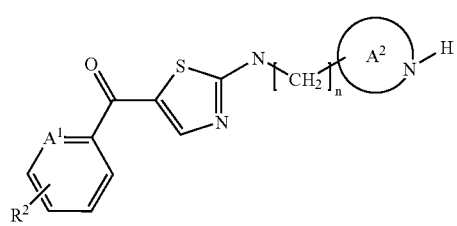

IE in the presence of a compound of formula

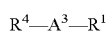    II in order to obtain a compound of formula I, wherein $R^1$ to $R^3$, $A^1$, $A^2$, $A^3$ and n are defined as before and $R^4$ is chloro or hydroxy. Preferred is the above process, wherein $R^4$ is chloro. Particularly preferred is the above process, wherein the reaction is performed in the presence or the absence of a solvent and in the presence of a base. Preferred solvents are e.g. DCM, chloroform, dioxane, MeOH and THF. Examples of preferred bases are triethylamine and diisopropylethylamine.

Preferred intermediates are:

{2-[(Piperidin-4-ylmethyl)-amino]-thiazol-5-yl}-o-tolyl-methanone; hydrochloride

[2-(2-Piperidin-2-yl-ethylamino)-thiazol-5-yl]-o-tolyl-methanone; hydrochloride (S)-2-{[5-(2-Ethyl-benzoyl)-thiazol-2-ylamino]-methyl}-pyrrolidine-1-carboxylic acid tert-butyl ester The compounds of formula I described above for use as therapeutically active substances are a further object of the invention.

Also an object of the invention are compounds described above for the production of medicaments for the prophylaxis and therapy of illnesses which are caused by disorders associated with the NPY receptor, particularly for the production of medicaments for the prophylaxis and therapy of arthritis, cardiovascular diseases, diabetes, renal failure and particularly eating disorders and obesity.

Likewise an object of the invention are pharmaceutical compositions containing a compound of formula I described above and a therapeutically inert carrier.

An object of the invention is also the use of the compounds described above for the production of medicaments, particularly for the treatment and prophylaxis of arthritis, cardiovascular diseases, diabetes, renal failure and particularly eating disorders and obesity.

A further object of the invention comprises compounds which are manufactured according to one of the described processes.

A further object of the invention is a method for the treatment and prophylaxis of arthritis, cardiovascular diseases, diabetes, renal failure and particularly eating disorders and obesity whereby an effective amount of a compound described above is administered.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

Also an object of the invention are compounds described above for the production of medicaments for the prophylaxis and therapy of alcoholism.

A further object of the invention is a method for the treatment and prophylaxis of alcoholism.

Assay Procedures

Cloning of Mouse NPY5 Receptor cDNAs

The full-length cDNA encoding the mouse NPY5 (mNPY5) receptor was amplified from mouse brain cDNA using specific primers, designed based on the published sequence, and Pfu DNA-Polymerase. The amplification product was subcloned into the mammalian expression vector pcDNA3 using Eco RI and XhoI restriction sites. Positive clones were sequenced and one clone, encoding the published sequence was selected for generation of stable cell clones.

Stable Transfection

Human embryonic kidney 293 (HEK293) cells were transfected with 10 μg mNPY5 DNA using the lipofectamine reagent. Two days after transfection, geneticin selection (1 mg/ml) was initiated and several stable clones were isolated. One clone was further used for pharmacological characterization.

Radioligand Competition Binding

Human embryonic kidney 293 cells (HEK293), expressing recombinant mouse NPY5-receptor (mNPY5) were broken by three freeze/thawing cycles in hypotonic Tris buffer (5 mM, pH 7.4, 1 mM $MgCl_2$), homogenized and centrifuged at 72,000×g for 15 min. The pellet was washed twice with 75 mM Tris buffer, pH 7.4, containing 25 mM $MgCl_2$ and 250 mM sucrose, 0.1 mM phenylmethylsulfonylfluoride and 0.1 mM 1,10-pheneanthrolin, resuspended in the same buffer and stored in aliquots at −80° C. Protein was determined according to the method of Lowry using bovine serum albumine (BSA) as a standard.

Radioligand competition binding assays were performed in 250 μl 25 mM Hepes buffer (pH 7.4, 2.5 mM $CaCl_2$, 1 mM $MgCl_2$, 1% bovine serum albumine, and 0.01% $NaN_3$ containing 5 μg protein, 100 pM [$^{125}$I]labelled peptide YY (PYY) and 10 μL DMSO containing increasing amounts of unlabelled test compounds. After incubation for 1 h at 22° C., bound and free ligand are separated by filtration over glass fibre filters. Non specific binding is assessed in the presence of 1 μM unlabelled PYY. Specific binding is defined as the difference between total binding and non specific binding. $IC_{50}$ values are defined as the concentration of antagonist that displaces 50% of the binding of [$^{125}$I] labelled neuropeptide Y. It is determined by linear regression analysis after logit/log transformation of the binding data.

Results obtained in the foregoing test using representative compounds of the invention as the test compounds are shown in the following table:

| Compound | NPY5-R (mouse) $IC_{50}$ (nM) |
|---|---|
| Example 18: 4-{[5-(2-Methyl-benzoyl)-thiazol-2-ylamino]-methyl}-piperidine-1-sulfonic acid dimethylamide | 0.85 |
| Example 32: (2-Ethyl-phenyl)-{2-[1-(thiophene-2-sulfonyl)-piperidin-4-ylamino]-thiazol-5-yl}-methanone | 0.75 |
| Example 41: {2-[1-(Thiophene-2-sulfonyl)-piperidin-4-ylamino]-thiazol-5-yl}-o-tolyl-methanone | 0.77 |

Compounds as described above have $IC_{50}$ values below 1000 nM; more preferred compounds have $IC_{50}$ values below 100 nM, particularly below 10 nM. Most preferred compounds have $IC_{50}$ values below 2 nM. These results have been obtained by using the foregoing test.

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example A 4-(3-Dimethylaminomethylene-thioureidomethyl)-piperidine-1-carboxylic acid tert-butyl ester

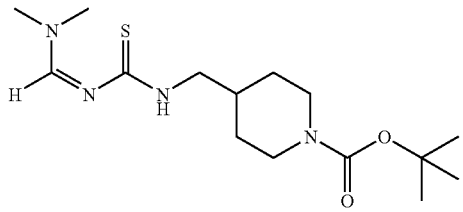

A solution of 17.7 g (82.6 mmol) 4-aminomethyl-piperidine-1-carboxylic acid tert-butyl ester (commercially available) in 150 ml THF was treated with 11.1 ml (82.6 mmol) benzoyl isothiocyanate and stirred for 1 h at room temperature. After evaporation of the solvents the residue was taken up in 100 ml MeOH and treated with 34.2 g (248 mmol) potassium carbonate in 100 ml water. After stirring the mixture for 16 h at room temperature all volatiles were removed and the residue extracted with ethyl acetate. The combined organic layers were washed with saturated NaHCO$_3$ solution and dried with MgSO$_4$. After evaporation of the volatiles 88.1 ml (661 mmol) N,N-dimethylformamide dimethyl acetal was added and the mixture was heated to 110° C. for 16 h. The precipitate was filtered off, washed with n-hexane and dried to yield 21.5 g (79%) of the title compound as pink amorphous solid.

MS (m/e): 329.4 (MH$^+$, 100%)

Example B

2-[2-(3-Dimethylaminomethylene-thioureido)-ethyl]-piperidine-1-carboxylic acid tert-butyl ester

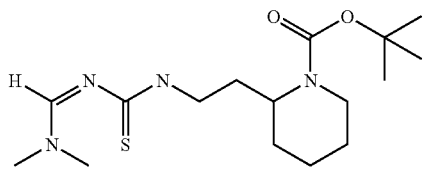

According to the procedure described for the synthesis of 4-(3-dimethylaminomethylene-thioureidomethyl)-piperidine-1-carboxylic acid tert-butyl ester (Example A), 2-[2-(3-dimethylaminomethylene-thioureido)-ethyl]-piperidine-1-carboxylic acid tert-butyl ester (Example B) was synthesised starting from 2-(2-amino-ethyl)-piperidine-1-carboxylic acid tert-butyl ester (commercially available).

MS (m/e): 343.4 (MH$^+$, 100%)

Example C

2-Bromo-1-(2-ethyl-phenyl)-ethanone

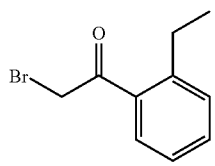

To a solution of 15.2 g (88 mmol) dibromethane in 120 ml THF at −75° C. was added 44 ml (88 mmol) of a 2M solution of LDA in THF and subsequently 6.57 g (40 mmol) ethylbenzoic acid methyl ester in 80 ml THF. 37.5 ml of a 1.6 M n-butyl lithium solution in n-hexane was added and after 30 min the mixture was treated carefully below −65° C. with 35 ml HCl (37%). The mixture was washed with water and NaHCO$_3$ aq. and the organic phase was dried with MgSO$_4$, filtered and concentrated under reduced pressure. The residue was purified by flash column chromatography on silica eluting with ethyl acetate/hexane 1:9 twice to afford 3.8 g (41%) of the title compound as yellow oil. MS (m/e): 227.1 (M+H, 100%).

Example D

{2-[(Piperidin-4-ylmethyl)-amino]-thiazol-5-yl}-o-tolyl-methanone; hydrochloride

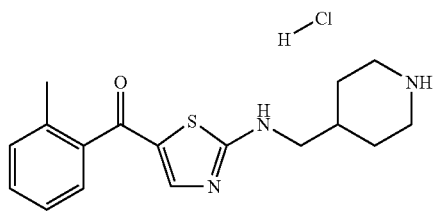

A mixture of 0.787 g (2.4 mmol) 4-(3-dimethylaminomethylene-thioureidomethyl)-piperidine-1-carboxylic acid tert-butyl ester, 0.61 g (2.88 mmol) 2-Bromo-1-o-tolyl-ethanone and 1002 ul (7.2 mmol) NEt$_3$ in 3 ml EtOH was heated to 90° C. for 16 h. After concentration under vacuum the mixture was treated with diluted aqueous diluted NaHCO$_3$ solution and extracted with ethyl acetate. The combined organic layers were filtered through a plug of silica topped with a layer of MgSO$_4$ and concentrated in vacuo to yield 707 mg (71%) of the intermediate 4-{[5-(2-Methyl-benzoyl)-thiazol-2-ylamino]methyl}-piperidine-1-carboxylic acid tert-butyl ester MS (m/e): 416.3 (MH$^+$, 100%). The residue was taken up in dioxane and 10 ml of a 4N HCl solution in dioxane was added. The mixture was stirred at room temperature for 16 h and evaporated to yield 598 mg (quant.) of the title compound.

MS (m/e): 315.7 (MH$^+$, 100%)

Example E

[2-(2-Piperidin-2-yl-ethylamino)-thiazol-5-yl]-o-tolyl-methanone; hydrochloride

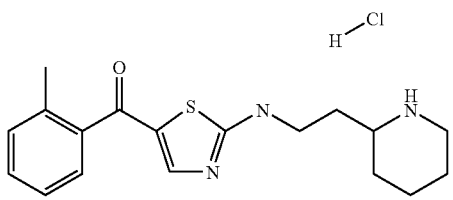

A mixture of 0.787 g (2.4 mmol) 2-[2-(3-dimethylaminomethylene-thioureido)-ethyl]-piperidine-1-carboxylic acid tert-butyl ester, 0.61 g (2.88 mmol) 2-Bromo-1-o-tolyl-ethanone and 1002 ul (7.2 mmol) NEt$_3$ in 3 ml EtOH was heated to 90° C. for 16 h. After concentration under vacuum the mixture was treated with diluted aqueous diluted NaHCO$_3$ solution and extracted with ethyl acetate. The combined organic layers were filtered through a plug of silica topped with a layer of MgSO$_4$ and concentrated in vacuo to yield 710 mg (69%) of the intermediate 2-{2-[5-(2-methyl-benzoyl)-thiazol-2-ylamino]-ethyl}-piperidine-1-carboxylic acid tert-butyl ester MS (m/e): 430.5 (MH$^+$, 100%). The residue was taken up in dioxane and 10 ml of a 4N HCl solution in dioxane was added. The mixture was stirred at room temperature for 16 h and evaporated to yield 606 mg (quant.) of the title compound.

MS (m/e): 329.8 (MH$^+$, 100%)

Example 1

(2-{[1-(Thiophene-2-sulfonyl)-piperidin-4-ylmethyl]-amino}-thiazol-5-yl)-o-tolyl-methanone A mixture of 35.2 mg (0.1 mmol) {2-[(piperidin-4-ylmethyl)-amino]-thiazol-5-yl}-o-tolyl-methanone; hydrochloride, 21.9 mg (0.12 mmol) thiophene-2-sulfonyl chloride (commercially available) and 44.6 ul (0.32 mmol) NEt$_3$ in a mixture of DCM/MeOH 3/1 was stirred at 60° C. for 16 h. After cooling to room temperature the mixture was concentrated and MeOH (1 ml) and formic acid (0.5 ml) was added and the mixture was subjected to reversed phase HPLC purification eluting with a gradient of acetonitrile/water. After evaporation of the product fractions 22 mg (48%) of the title compound was obtained.

MS (m/e): 460.2 (MH$^-$, 100%)

Examples 2 to 19 have been prepared according to the procedure described for the synthesis of Example 1. The corresponding starting materials are mentioned in table 1.

Example 20

(2-{2-[1-(Thiophene-3-sulfonyl)-piperidin-2-yl]-ethylamino}-thiazol-5-yl)-o-tolyl-methanone A mixture of 35.2 mg (0.1 mmol) [2-(2-Piperidin-2-yl-ethylamino)-thiazol-5-yl]-o-tolyl-methanone; hydrochloride, 21.9 mg (0.12 mmol) thiophene-3-sulfonyl chloride (commercially available) and 44.6 ul (0.32 mmol) NEt$_3$ in a mixture of DCM/MeOH 3/1 was stirred at 60° C. for 16 h. After cooling to room temperature the mixture was concentrated and MeOH (1 ml) and formic acid (0.5 ml) was added and the mixture was subjected to reversed phase HPLC purification eluting with a gradient of acetonitrile/water. After evaporation of the product fractions 7 mg (15%) of the title compound was obtained. MS (m/e): 474.0 (MH$^-$, 100%)

Example 21

(2-{2-[1-(3-Fluoro-benzenesulfonyl)-piperidin-2-yl]-ethylamino}-thiazol-5-yl)-o-tolyl -methanone According to the procedure described for the synthesis of Example 20, (2-{2-[1-(3-fluoro -benzenesulfonyl)-piperidin-2-yl]-ethylamino}-thiazol-5-yl)-o-tolyl-methanone was synthesised from [2-(2-piperidin-2-yl-ethylamino)-thiazol-5-yl]-o-tolyl-methanone; hydrochloride and 3-fluorophenyl-sulfonyl chloride. MS (m/e): 486.2 (MH$^-$, 100%)

Example F 2-(S)-(3-Dimethylaminomethylene-thioureidomethyl)-pyrrolidine-1-carboxylic acid 1,1-dimethylethyl ester

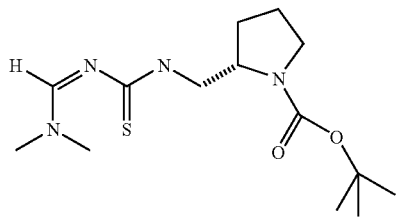

2-(S)-(3-dimethylaminomethylene-thioureidomethyl)-pyrrolidine-1-carboxylic acid 1,1-dimethylethyl ester was prepared from (S)-2-(aminomethyl)-1-pyrrolidinecarboxylic acid 1,1-dimethylethyl ester according to the procedure described in Example A (4-(3-dimethylaminomethylene -thioureidomethyl)-piperidine-1-carboxylic acid tert-butyl ester). Purified by column chromatography on silica gel (2:1 to 3:1 ethyl acetate/hexane eluant). Yellow solid. MS: 315.4 (M+H)$^+$

Example G 4-(3-Dimethylaminomethylene-thioureido)-piperidine-1-carboxylic acid 1,1-dimethylethyl ester

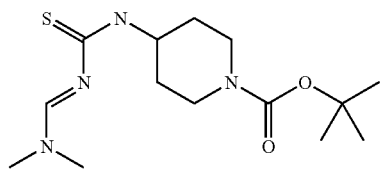

4-(3-Dimethylaminomethylene-thioureido)-piperidine-1-carboxylic acid 1,1-dimethylethyl ester was prepared from 4-amino-1-piperidinecarboxylic acid 1,1-dimethylethyl ester according to the procedure described in example A(4-(3-dimethylaminomethylene-thioureidomethyl)-piperidine-1-carboxylic acid tert-butyl ester) White solid. Mp 170° C.; MS: 315.4 (M+H)$^+$

Example 22

(S)-2-{[5-(2-Ethyl-benzoyl)-thiazol-2-ylamino]-methyl}-pyrrolidine-1-carboxylic acid tert-butyl ester To a solution of 2-(S)-(3-dimethylaminomethylene-thioureidomethyl)-pyrrolidine-1-carboxylic acid 1,1-dimethylethyl ester (150 mg) in N,N-dimethylformamide (2 ml) was added 2-bromo-1-(2-ethylphenyl)-ethanone (109 mg). The mixture was stirred 65 h at room temperature, diluted with dichloromethane, washed twice with water, once with brine, dried over magnesium sulfate and evaporated under reduced pressure. The residue was purified by column chromatography on silica gel (2:1 ethyl acetate/hexane eluant) to afford the product as yellow oil (129 mg, 65%).

Examples 23 and 27 to 30 have been prepared according to the procedure described for the synthesis of Example 1. The corresponding starting materials are mentioned in table 1.

Example 24

(S)-(2-Ethyl-phenyl)-(2-{[1-(thiophene-2-sulfonyl)-pyrrolidin-2-ylmethyl]-amino}-thiazol-5-yl)-methanone (S)-2-{[5-(2-Ethyl-benzoyl)-thiazol-2-ylamino]-methyl}-pyrrolidine-1-carboxylic acid tert-butyl ester (50 mg) was dissolved in dioxane (2 ml) and the solution cooled to 0° C. (ice-bath) before the addition of 25% aqueous hydrochloric acid (0.2 ml). The solution was stirred 4 h at room temperature and evaporated to dryness. The residue was dissolved in dichloromethane (2 ml), triethylamine (0.02 ml) added followed by a solution of thiophene-2-sulfonyl chloride (23 mg) in dichloromethane (0.5 ml). The mixture was stirred 5 h at room temperature, diluted with dichloromethane, washed with water, dried over magnesium sulphate and evaporated. The residue was purified by column chromatography on silica gel (5:1 to 1:0 ethyl acetate/hexane) to afford the product as an off-white foam (36 mg, 65%).

Examples 25, 26 and 31 to 42 have been prepared according to the procedure described for the synthesis of Example 24. The corresponding starting materials are mentioned in table 1.

TABLE 1

| No | MW | name | Starting materials | MW found |
|---|---|---|---|---|
| 1 | 461.6 | (2-{[1-(Thiophene-2-sulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and Thiophene-2-sulfonyl chloride (commercially available) | 460.2 (M − H)⁻ |
| 2 | 461.6 | (2-{[1-(Thiophene-3-sulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and Thiophene-3-sulfonyl chloride (commercially available) | 460.2 (M − H) |
| 3 | 496.1 | (2-{[1-(5-Chloro-thiophene-2-sulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and 5-Chloro-thiophene-2-sulfonyl chloride (commercially available) | 494.0 (M − H) |
| 4 | 473.6 | (2-{[1-(2-Fluoro-benzenesulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and 2-Fluoro-benzenesulfonyl chloride (commercially available) | 472.1 (M − H) |
| 5 | 473.6 | (2-{[1-(3-Fluoro-benzenesulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and 3-Fluoro-benzenesulfonyl chloride (commercially available) | 472.1 (M − H) |
| 6 | 473.6 | (2-{[1-(4-Fluoro-benzenesulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and 4-Fluoro-benzenesulfonyl chloride (commercially available) | 472.0 (M − H) |

TABLE 1-continued

| No | MW | name | Starting materials | MW found |
|---|---|---|---|---|
| 7 | 491.6 | (2-{1-(2,4-Difluoro-benzenesulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and 2,4-Difluoro-benzenesulfonyl chloride (commercially available) | 490.1 (M − H) |
| 8 | 469.6 | (2-{1-(Toluene-2-sulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and 2-Methyl-benzenesulfonyl chloride (commercially available) | 468.1 (M − H) |
| 9 | 483.7 | (2-{1-(2,5-Dimethyl-benzenesulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and 2,5-Dimethyl-benzenesulfonyl chloride (commercially available) | 482.3 (M − H) |
| 10 | 487.6 | (2-{1-(5-Fluoro-2-methyl-benzenesulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and 5-Fluoro-2-methyl-benzenesulfonyl chloride (commercially available) | 486.2 (M − H) |
| 11 | 485.6 | (2-{1-(3-Methoxy-benzenesulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and 3-Methoxy-benzenesulfonyl chloride (commercially available) | 484.2 (M − H) |
| 12 | 485.6 | (2-{1-(4-Methoxy-benzenesulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and 4-Methoxy-benzenesulfonyl chloride (commercially available) | 484.2 (M − H) |
| 13 | 539.6 | o-Tolyl-(2-{1-(4-trifluoromethoxy-benzenesulfonyl)-piperidin-4-ylmethyl]-amino}-thiazol-5-yl)-methanone | {2-[(Piperidin-4-ylmethyl)-amino]-thiazol-5-yl}-o-tolyl-methanone; hydrochloride and 4-Trifluoromehyloxy-benzenesulfonyl chloride (commercially available) | 538.0 (M − H) |
| 14 | 558 | (2-{1-(2-Chloro-4-trifluoromethyl-benzenesulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and 2-Chloro-4-trifluoromethyl-benzenesulfonyl chloride (commercially available) | 555.9 (M − H) |
| 15 | 490 | (2-{1-(4-Chloro-benzenesulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and 4-Chloro-benzenesulfonyl chloride (commercially available) | 488.1 (M − H) |
| 16 | 500.6 | (2-{1-(4-Nitro-benzenesulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and 4-Nitro-benzenesulfonyl chloride (commercially available) | 499.1 (M − H) |
| 17 | 448.6 | (2-{1-(Pyrrolidine-1-sulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and Pyrrolidine-1-sulfonyl chloride (commercially available) | 447.2 (M − H) |

TABLE 1-continued

| No | MW | name | Starting materials | MW found |
|---|---|---|---|---|
| 18 | 422.6 | 4-{[5-(2-Methyl-benzoyl)-thiazol-2-ylamino]-methyl}-piperidine-1-sulfonic acid dimethylamide | {2-[(Piperidin-4-ylmethyl)-amino]-thiazol-5-yl}-o-tolyl-methanone; hydrochloride and Dimethylamine-1-sulfonyl chloride (commercially available) | 421.2 (M − H) |
| 19 | 464.6 | (2-{1-(Morpholine-4-sulfonyl)-piperidin-4-ylmethyl]-amino}-thiazol-5-yl)-o-tolyl-methanone | {2-[(Piperidin-4-ylmethyl)-amino]-thiazol-5-yl}-o-tolyl-methanone; hydrochloride and Morpholine-1-sulfonyl chloride (commercially available) | 463.2 (M − H) |
| 20 | 475.7 | (2-{2-[1-(Thiophene-3-sulfonyl)-piperidin-2-yl]-ethylamino}-thiazol-5-yl)-o-tolyl-methanone | [2-(2-Piperidin-2-yl-ethylamino)-thiazol-5-yl]-o-tolyl-methanone; hydrochloride and Thiophene-3-sulfonyl chloride (commercially available) | 474.0 (M − H) |
| 21 | 487.6 | (2-{2-[1-(3-Fluoro-benzenesulfonyl)-piperidin-2-yl]-ethylamino}-thiazol-5-yl)-o-tolyl-methanone | [2-(2-Piperidin-2-yl-ethylamino)-thiazol-5-yl]-o-tolyl-methanone; hydrochloride and 3-Fluoro-benzenesulfonyl chloride (commercially available) | 486.2 (M − H) |
| 22 | 415.6 | (S)-2-{[5-(2-Ethyl-benzoyl)-thiazol-2-ylamino]-methyl}-pyrrolidine-1-carboxylic acid tert-butyl ester | 2-(S)-(3-Dimethylaminomethylene-thioureidomethyl)-pyrrolidine-1-carboxylic acid 1,1-dimethylethyl ester and 2-bromo-1-(2-ethylphenyl)-ethanone | 416.3 (M + H)+ |
| 23 | 455.5 | (S)-2-{[5-(2-Trifluoromethyl-benzoyl)-thiazol-2-ylamino]-methyl}-pyrrolidine-1-carboxylic acid tert-butyl ester | 2-(S)-(3-Dimethylaminomethylene-thioureidomethyl)-pyrrolidine-1-carboxylic acid 1,1-dimethylethyl ester and 2-bromo-1-(2-trifluoromethylphenyl)-ethanone | 456.5 (M + H)+ |
| 24 | 461.6 | (S)-(2-Ethyl-phenyl)-(2-{[1-(thiophene-2-sulfonyl)-pyrrolidin-2-ylmethyl]-amino}-thiazol-5-yl)-methanone | (S)-2-{[5-(2-Ethyl-benzoyl)-thiazol-2-ylamino]-methyl}-pyrrolidine-1-carboxylic acid 1,1-dimethylethyl ester and thiophene-2-sulfonyl chloride | 462.2 (M + H)+ |
| 25 | 501.6 | (S)-(2-{[1-(Thiophene-2-sulfonyl)-pyrrolidin-2-ylmethyl]-amino}-thiazol-5-yl)-(2-trifluoromethyl-phenyl)-methanone | (S)-2-{[5-(2-Trifluoromethyl-benzoyl)-thiazol-2-ylamino]-methyl}-pyrrolidine-1-carboxylic acid 1,1-dimethylethyl 1 ester and thiophene-2-sulfonyl chloride | 502.2 (M + H)+ |
| 26 | 545.6 | (S)-(2-{[1-(Naphthalene-1-sulfonyl)-pyrrolidin-2-ylmethyl]-amino}-thiazol-5-yl)-(2-trifluoromethyl-phenyl)-methanone | (S)-2-{[5-(2-Trifluoromethyl-benzoyl)-thiazol-2-ylamino]-methyl}-pyrrolidine-1-carboxylic acid 1,1-dimethylethyl ester and naphthalene-1-sulfonyl chloride | 546.2 (M + H)+ |
| 27 | 415.6 | 4-[5-(2-Ethyl-benzoyl)-thiazol-2-ylamino]-piperidine-1-carboxylic acid tert-butyl ester | 4-(3-Dimethylaminomethylene-thioureido)-piperidine-1-carboxylic acid 1,1-dimethylethyl ester and 2-bromo-1-(2-ethylphenyl)-ethanone | 416.3 (M + H)+ |

TABLE 1-continued

| No | MW | name | Starting materials | MW found |
|---|---|---|---|---|
| 28 | 401.5 | 4-[5-(2-Methyl-benzoyl)-thiazol-2-ylamino]-piperidine-1-carboxylic acid tert-butyl ester | 4-(3-Dimethylaminomethylene-thioureido)-piperidine-1-carboxylic acid 1,1-dimethylethyl ester and 2-bromo-1-(2-methylphenyl)-ethanone | 402.5 (M + H)+ |
| 29 | 455.5 | 4-[5-(2-Trifluoromethyl-benzoyl)-thiazol-2-ylamino]-piperidine-1-carboxylic acid tert-butyl ester | 4-(3-Dimethylaminomethylene-thioureido)-piperidine-1-carboxylic acid 1,1-dimethylethyl ester and 2-bromo-1-(2-trifluoromethylphenyl)-ethanone | 456.4 (M + H)+ |
| 30 | 388.5 | 4-[5-(Pyridine-2-carbonyl)-thiazol-2-ylamino]-piperidine-1-carboxylic acid tert-butyl ester | 4-(3-Dimethylaminomethylene-thioureido)-piperidine-1-carboxylic acid 1,1-dimethylethyl ester and 2-bromo-1-(2-pyridinyl)-ethanone | 389.2 (M + H)+ |
| 31 | 505.7 | (2-Ethyl-phenyl)-{2-[1-(naphthalene-1-sulfonyl)-piperidin-4-ylamino]-thiazol-5-yl}-methanone | 4-[5-(2-Ethyl-benzoyl)-thiazol-2-ylamino]-piperidine-1-carboxylic acid 1,1-dimethylethyl ester and naphthalene-1-sulfonyl chloride | 506.3 (M + H)+ |
| 32 | 461.6 | (2-Ethyl-phenyl)-{2-[1-(thiophene-2-sulfonyl)-piperidin-4-ylamino]-thiazol-5-yl}-methanone | 4-[5-(2-Ethyl-benzoyl)-thiazol-2-ylamino]-piperidine-1-carboxylic acid 1,1-dimethylethyl ester and thiophene-2-sulfonyl chloride | 462.2 (M + H)+ |
| 33 | 499.7 | (2-Ethyl-phenyl)-{2-[1-(2-methoxy-5-methyl-benzenesulfonyl)-piperidin-4-ylamino]-thiazol-5-yl}-methanone | 4-[5-(2-Ethyl-benzoyl)-thiazol-2-ylamino]-piperidine-1-carboxylic acid 1,1-dimethylethyl ester and 2-methoxy-5-methyl-benzenesulfonyl chloride | 500.3 (M + H)+ |
| 34 | 478.6 | {2-[1-(Naphthalene-1-sulfonyl)-piperidin-4-ylamino]-thiazol-5-yl}-pyridin-2-yl-methanone | 4-[5-(Pyridine-2-carbonyl)-thiazol-2-ylamino]-piperidine-1-carboxylic acid 1,1-dimethylethyl ester and naphthalene-1-sulfonyl chloride | 479.3 (M + H)+ |
| 35 | 434.6 | Pyridin-2-yl-{2-[1-(thiophene-2-sulfonyl)-piperidin-4-ylamino]-thiazol-5-yl}-methanone | 4-[5-(Pyridine-2-carbonyl)-thiazol-2-ylamino]-piperidine-1-carboxylic acid 1,1-dimethylethyl ester and thiophene-2-sulfonyl chloride | 435.3 (M + H)+ |
| 36 | 472.6 | {2-[1-(2-Methoxy-5-methyl-benzenesulfonyl)-piperidin-4-ylamino]-thiazol-5-yl}-pyridin-2-yl-methanone | 4-[5-(Pyridine-2-carbonyl)-thiazol-2-ylamino]-piperidine-1-carboxylic acid 1,1-dimethylethyl ester and 2-methoxy-5-methyl-benzenesulfonyl chloride | 473.2 (M + H)+ |
| 37 | 545.6 | {2-[1-(Naphthalene-1-sulfonyl)-piperidin-4-ylamino]-thiazol-5-yl}-(2-trifluoromethyl-phenyl)-methanone | 4-[5-(2-Trifluoromethyl-benzoyl)-thiazol-2-ylamino]-piperidine-1-carboxylic acid 1,1-dimethylethyl ester and naphthalene-1-sulfonyl chloride | 546.3 (M + H)+ |
| 38 | 501.6 | {2-[1-(Thiophene-2-sulfonyl)-piperidin-4-ylamino]-thiazol-5-yl}-(2-trifluoromethyl-phenyl)-methanone | 4-[5-(2-Trifluoromethyl-benzoyl)-thiazol-2-ylamino]-piperidine-1-carboxylic acid 1,1-dimethylethyl ester and thiophene-2-sulfonyl chloride | 502.1 (M + H)+ |

TABLE 1-continued

| No | MW | name | Starting materials | MW found |
|----|------|------|--------------------|----------|
| 39 | 539.6 | {2-[1-(2-Methoxy-5-methyl-benzenesulfonyl)-piperidin-4-ylamino]-thiazol-5-yl}-(2-trifluoromethyl-phenyl)-methanone | 4-[5-(2-Trifluoromethyl-benzoyl)-thiazol-2-ylamino]-piperidine-1-carboxylic acid 1,1-dimethylethyl ester and 2-methoxy-5-methyl-benzenesulfonyl chloride | 540.3 (M + H)+ |
| 40 | 491.6 | {2-[1-(Naphthalene-1-sulfonyl)-piperidin-4-ylamino]-thiazol-5-yl}-o-tolyl-methanone | 4-[5-(2-Methyl-benzoyl)-thiazol-2-ylamino]-piperidine-1-carboxylic acid 1,1-dimethylethyl ester and naphthalene-1-sulfonyl chloride | 492.2 (M + H)+ |
| 41 | 447.6 | {2-[1-(Thiophene-2-sulfonyl)-piperidin-4-ylamino]-thiazol-5-yl}-o-tolyl-methanone | 4-[5-(2-Methyl-benzoyl)-thiazol-2-ylamino]-piperidine-1-carboxylic acid 1,1-dimethylethyl ester and thiophene-2-sulfonyl chloride | 448.2 (M + H)+ |
| 42 | 485.6 | {2-[1-(2-Methoxy-5-methyl-benzenesulfonyl)-piperidin-4-ylamino]-thiazol-5-yl}-o-tolyl-methanone | 4-[5-(2-Methyl-benzoyl)-thiazol-2-ylamino]-piperidine-1-carboxylic acid 1,1-dimethylethyl ester and 2-methoxy-5-methyl-benzenesulfonyl chloride | 486.3 (M + H)+ |

Example A

A compound of formula I can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

What is claimed is:

1. A compound of formula I

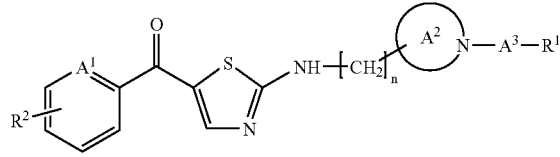

(I)

wherein $R^1$ is selected from the group consisting of aryl; substituted aryl; heterocyclyl which is a 5- to 10-membered heterocyclic ring which has at least one ring hetero atom selected from nitro, oxygen and sulfur; substituted heterocyclyl; amino; and alkoxy; wherein substituted aryl is aryl which is substituted with a group selected from the group consisting of halogen, trifluoromethyl, trifluoromethoxy, amino, alkyl, cycloalkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-$SO_2$—, amino-$SO_2$—, and cycloalkyl, and wherein substituted heterocyclyl is heterocyclyl which is substituted on at least one carbon atom with a group selected from the group consisting of cyano, trifluoromethyl, trifluoromethoxy, alkyl-$SO_2$—, amino-$SO_2$—, halogen, alkoxy, hydroxy, amino, cycloalkyl, alkylcarbonyl, aminocarbonyl nitro, alkyl, and alkoxycarbonyl;

$R^2$ is hydrogen, alkyl or halogen;

$R^3$ is alkyl, halogen or trifluoromethyl;

$A^1$ is C-$R^3$ or nitrogen;

A² is piperidine or pyrrolidine, wherein the nitrogen atom of the piperidine and pyrrolidine ring is attached to A³;
A³ is —S(O)₂— or —C(O)—;
n is zero, 1 or 2;
or a pharmaceutically acceptable salt or ester thereof.

2. The compound according to claim 1, wherein R¹ is selected from the group consisting of naphthyl, pyrrolidinyl, dialkylamino, morpholinyl, alkoxy, phenyl, substituted phenyl, thiophenyl and substituted thiophenyl, wherein substituted phenyl and substituted thiophenyl are phenyl and thiopenyl, respectively, each of which are substituted with one to three substituents independently selected from alkyl, alkoxy, trifluoromethyl, trifluoromethoxy, nitro and halogen.

3. The compound according to claim 2, wherein R¹ is selected from the group consisting of thiophenyl, chlorothiophenyl, naphthyl, pyrrolidinyl, dimethylamino, morpholinyl, tert-butoxy and substituted phenyl which is phenyl substituted with one or two substituents independently selected from fluoro, chloro, methyl, ethyl, methoxy, ethoxy, trifluoromethoxy, trifluoromethyl and nitro.

4. The compound according to claim 1, wherein R¹ is amino or alkoxy.

5. The compound according to claim 4, wherein R¹ is amino which is —N(CH₃)CH₃.

6. The compound according to claim 1, wherein R² is hydrogen.

7. The compound according to claim 1, wherein A¹ is nitrogen.

8. The compound according to claim 1, wherein A¹ is C—R³.

9. The compound according to claim 8, wherein R³ is methyl, ethyl or trifluoromethyl.

10. The compound according to claim 1, wherein A³ is —S(O)₂—.

11. The compound according to claim 1, wherein A³ is —C(O)—.

12. The compound according to claim 1, wherein A² is piperidine, wherein the nitrogen atom of the piperidine ring is attached to A³.

13. The compound according to claim 1, wherein A² is pyrrolidine, wherein the nitrogen atom of the pyrrolidine ring is attached to A³.

14. The compound according to claim 1, wherein n is zero or 1.

15. The compound according to claim 1, selected from the group consisting of:
(2-{[1-(thiophene-2-sulfonyl)-piperidin-4-ylmethyl]-amino}-thiazol-5-yl)-o-tolyl-methanone;
(2-{[1-(thiophene-3-sulfonyl)-piperidin-4-ylmethyl]-amino}-thiazol-5-yl)-o-tolyl-methanone;
(2-{[1-(5-chloro-thiophene-2-sulfonyl)-piperidin-4-ylmethyl]-amino}-thiazol-5-yl)-o-tolyl-methanone;
(2-{[1-(2-fluoro-benzenesulfonyl)-piperidin-4-ylmethyl]-amino}-thiazol-5-yl)-o-tolyl-methanone;
(2-{[1-(3-fluoro-benzenesulfonyl)-piperidin-4-ylmethyl]-amino}-thiazol-5-yl)-o-tolyl-methanone;
(2-{[1-(4-fluoro-benzenesulfonyl)-piperidin-4-ylmethyl]-amino}-thiazol-5-yl)-o-tolyl-methanone;
(2-{[1-(2,4-difluoro-benzenesulfonyl)-piperidin-4-ylmethyl]-amino}-thiazol-5-yl)-o-tolyl-methanone;
(2-{[1-(toluene-2-sulfonyl)-piperidin-4-ylmethyl]-amino}-thiazol-5-yl)-o-tolyl-methanone;
(2-{[1-(2,5-dimethyl-benzenesulfonyl)-piperidin-4-ylmethyl]-amino}-thiazol-5-yl)-o-tolyl-methanone; and
(2-{[1-(5-fluoro-2-methyl-benzenesulfonyl)-piperidin-4-ylmethyl]-amino}-thiazol-5-yl)-o-tolyl-methanone;
or a pharmaceutically acceptable salt thereof.

16. The compound according to claim 1, selected from the group consisting of:
(2-{[1-(3-methoxy-benzenesulfonyl)-piperidin-4-ylmethyl]-amino}-thiazol-5-yl)-o-tolyl-methanone;
(2-{[1-(4-methoxy-benzenesulfonyl)-piperidin-4-ylmethyl]-amino}-thiazol-5-yl)-o-tolyl-methanone;
o-tolyl-(2-{[1-(4-trifluoromethoxy-benzenesulfonyl)-piperidin-4-ylmethyl]-amino}-thiazol-5-yl)-methanone;
(2-{[1-(2-chloro-4-trifluoromethyl-benzenesulfonyl)-piperidin-4-ylmethyl]-amino}-thiazol-5-yl)-o-tolyl-methanone;
(2-{[1-(4-chloro-benzenesulfonyl)-piperidin-4-ylmethyl]-amino}-thiazol-5-yl)-o-tolyl-methanone;
(2-{[1-(4-nitro-benzenesulfonyl)-piperidin-4-ylmethyl]-amino}-thiazol-5-yl)-o-tolyl-methanone;
(2-{[1-(pyrrolidine-1-sulfonyl)-piperidin-4-ylmethyl]-amino}-thiazol-5-yl)-o-tolyl-methanone;
(2-{[1-(morpholine-4-sulfonyl)-piperidin-4-ylmethyl]-amino}-thiazol-5-yl)-o-tolyl-methanone; and
(2-{2-[1-(thiophene-3-sulfonyl)-piperidin-2-yl]-ethylamino}-thiazol-5-yl)-o-tolyl-methanone;
or a pharmaceutically acceptable salt thereof.

17. The compound according to claim 1, selected from the group consisting of:
(2-{2-[1-(3-fluoro-benzenesulfonyl)-piperidin-2-yl]-ethylamino}-thiazol-5-yl)-o-tolyl-methanone;
(S)-2-{[5-(2-ethyl-benzoyl)-thiazol-2-ylamino]-methyl}-pyrrolidine-1-carboxylic acid tert-butyl ester;
(S)-2-{[5-(2-trifluoromethyl-benzoyl)-thiazol-2-ylamino]-methyl}-pyrrolidine-1-carboxylic acid tert-butyl ester;
(S)-(2-ethyl-phenyl)-(2-{[1-(thiophene-2-sulfonyl)-pyrrolidin-2-ylmethyl]-amino}-thiazol-5-yl)-methanone;
(S)-(2-{[1-(thiophene-2-sulfonyl)-pyrrolidin-2-ylmethyl]-amino}-thiazol-5-yl)-(2-trifluoromethyl-phenyl)-methanone;
(S)-(2-{[1-(naphthalene-1-sulfonyl)-pyrrolidin-2-ylmethyl]-amino}-thiazol-5-yl)-(2-trifluoromethyl-phenyl)-methanone;
4-[5-(2-ethyl-benzoyl)-thiazol-2-ylamino]-piperidine-1-carboxylic acid tert-butyl ester;
4-[5-(2-methyl-benzoyl)-thiazol-2-ylamino]-piperidine-1-carboxylic acid tert-butyl ester;
4-[5-(2-trifluoromethyl-benzoyl)-thiazol-2-ylamino]-piperidine-1-carboxylic acid tert-butyl ester; and
4-[5-(pyridine-2-carbonyl)-thiazol-2-ylamino]-piperidine-1-carboxylic acid tert-butyl ester;
or a pharmaceutically acceptable salt thereof.

18. The compound according to claim 1, selected from the group consisting of:
(2-ethyl-phenyl)-{2-[1-(naphthalene-1-sulfonyl)-piperidin-4-ylamino]-thiazol-5-yl}-methanone;
(2-ethyl-phenyl)-{2-[1-(2-methoxy-5-methyl-benzenesulfonyl)-piperidin-4-ylamino]-thiazol-5-yl}-methanone;
{2-[1-(naphthalene-1-sulfonyl)-piperidin-4-ylamino]-thiazol-5-yl}-pyridin-2-yl-methanone;
pyridin-2-yl-{2-[1-(thiophene-2-sulfonyl)-piperidin-4-ylamino]-thiazol-5-yl}-methanone;
{2-[1-(2-methoxy-5-methyl-benzenesulfonyl)-piperidin-4-ylamino]-thiazol-5-yl}-pyridin-2-yl-methanone;
{2-[1-(naphthalene-1-sulfonyl)-piperidin-4-ylamino]-thiazol-5-yl}-(2-trifluoromethyl-phenyl)-methanone;
{2-[1-(thiophene-2-sulfonyl)-piperidin-4-ylamino]-thiazol-5-yl}-(2-trifluoromethyl-phenyl)-methanone;
{2-[1-(2-methoxy-5-methyl-benzenesulfonyl)-piperidin-4-ylamino]-thiazol-5-yl}-(2-trifluoromethyl-phenyl)-methanone;

{2-[1-(naphthalene-1-sulfonyl)-piperidin-4-ylamino]-thiazol-5-yl}-o-tolyl-methanone; and
{2-[1-(2-methoxy-5-methyl-benzenesulfonyl)-piperidin-4-ylamino]-thiazol-5-yl}-o-tolyl-methanone;
or a pharmaceutically acceptable salt thereof.

19. The compound according to claim 1, which is 4-{[5-(2-methyl-benzoyl)-thiazol-2-ylamino]-methyl}-piperidine-1-sulfonic acid dimethylamide;
or a pharmaceutically acceptable salt thereof.

20. The compound according to claim 1, which is: (2-ethyl-phenyl)-{2-[1-(thiophene-2-sulfonyl)-piperidin-4-ylamino]-thiazol-5-yl}-methanone;
or a pharmaceutically acceptable salt thereof.

21. The compound according to claim 1, which is: {2-[1-(thiophene-2-sulfonyl)-piperidin-4-ylamino]-thiazol-5-yl}-o-tolyl-methanone;
or a pharmaceutically acceptable salt thereof.

22. A pharmaceutical composition comprising a compound in accordance with claims 1 or a pharmaceutically acceptable salt or ester thereof, and a therapeutically inert carrier.

23. A method for the treatment of obesity in a patient in need thereof, which comprises administering an effective amount of a compound of claim 1 or a pharmaceutically acceptable salt or ester thereof to said patient.

24. The method for treatment of obesity according to claim 23, further comprising administering to the patient a therapeutically effective amount of orlistat.

25. The method according to claim 24 for simultaneous, separate or sequential administration.

26. The pharmaceutical composition of claim 22 further comprising orlistat.

27. The compound of formula I according to claim 1 or a pharmaceutically acceptable salt thereof.

28. The pharmaceutical composition according to claim 22, consisting essentially of a compound in accordance with claim 1 or a pharmaceutically acceptable salt thereof.

29. The method for the treatment of obesity according to claim 23, comprising administering an effective amount of a compound of claim 1 or a pharmaceutically acceptable salt thereof.

* * * * *